US005837449A

United States Patent [19]
Monia et al.

[11] Patent Number: 5,837,449
[45] Date of Patent: Nov. 17, 1998

[54] COMPOSITIONS AND METHODS FOR MODULATING β-AMYLOID

[75] Inventors: Brett P. Monia, Carlsbad; Susan M. Freier, San Diego; David J. Ecker, Leucadia, all of Calif.

[73] Assignee: Isis Pharmaceuticals, Inc., Carlsbad, Calif.

[21] Appl. No.: 331,389

[22] Filed: Oct. 28, 1994

Related U.S. Application Data

[63] Continuation-in-part of Ser. No. 814,963, Dec. 24, 1991, abandoned.

[51] Int. Cl.$^6$ .............................. C12Q 1/68; C07H 21/02
[52] U.S. Cl. ............................................. 435/6; 536/24.1
[58] Field of Search .................... 435/6, 91.2; 536/24.3, 536/24.31, 24.33, 24.5; 514/44

[56] References Cited

U.S. PATENT DOCUMENTS

| | | | |
|---|---|---|---|
| 4,358,535 | 11/1982 | Falkow et al. | 435/5 |
| 4,507,433 | 3/1985 | Miller et al. | 525/54.11 |
| 4,581,333 | 4/1986 | Kourilsky et al. | 435/6 |
| 4,689,320 | 8/1987 | Kaji | 514/44 |
| 4,806,463 | 2/1989 | Goodchild et al. | 435/5 |
| 4,958,013 | 9/1990 | Letsinger | 536/27 |
| 4,999,421 | 3/1991 | Brunck et al. | 530/350 |
| 5,004,810 | 4/1991 | Draper | 536/27 |
| 5,015,570 | 5/1991 | Scangos et al. | 435/6 |
| 5,034,506 | 7/1991 | Summerton et al. | 528/391 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,166,195 | 11/1992 | Ecker | 514/44 |
| 5,194,428 | 3/1993 | Agrawal et al. | 514/44 |
| 5,242,906 | 9/1993 | Pagano et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,455,169 | 10/1995 | Mullan | 435/240.2 |

FOREIGN PATENT DOCUMENTS

| | | |
|---|---|---|
| 0274826 A1 | 7/1988 | European Pat. Off. |
| 89/05358 | 6/1989 | WIPO |
| 91/04339 | 4/1991 | WIPO |
| 92/13069 | 8/1992 | WIPO |

OTHER PUBLICATIONS

Antiviral Agents Bulletin 5 161–163 year ?.

Askanas et al., "β–Amyloid Precursor Epitopes in Muscle Fibers of Inclusion Body Myositis", Ann. Neurol. 34:55–560 (1993).

Ausubel et al., "Identification of Newly Transcribed RNA", Current Protocols in Molecular Biology 1:4.10 –14.10.11 (1994).

Burch et al., "Oligonscleotides Antisense to the Interleukin 1 Receptor mRNA Block the Effects of Interleukin 1 in Cultured Murine and Human Fibroblasts and in Mice". J.Clin.Invest. 88:1190–1196 (1991).

Burdick et al., "Assembly and Aggregation Properties of Synthetic Alzheimer's A4/β Amyloid Peptide Analogs", J.Biol.Chem. 267:546–554 (1992).

Cai et al., "Release of Excess Amyloid β Protein from a Mutant Amyloid β Protein Precursor", Science 259:514–516 (1993).

Citron et al., "Mutation of the β–amyloid precursor protein in familial Alzheimer's disease increases β–protein production", Nature 360:672–674 (1992).

Ettinger et al., "Intrathecal Methotrexate Overdose Without Neurotoxicity", Cancer 41:1270–1273 (1978).

Goate et al., "Segregation of a Missense Mutation in the Amyloid Precursor Protein Gene with Familal Alzheimer's Disease", Nature 349:704–706 (1991).

Haan et al., "Amyloid in central nervous system disease", Clin.Neurol.Neurosurg. 92–4:305–310 (1990).

Higgins et al., "Antisense Inhibition of the p65 Subunit of NF–κB Blocks Tumorigenicity and Causes Tumor Regression", Proc.Natl.Acad.Sci. USA 90:9901–9905 (1993).

Kang et al., "The precursor of Alzheimer's disease amyloid A4 protein resembles a cell–surface receptor", Nature 325:733–736 (1987).

Kitajima et al., "Ablation of Transplanted HTLV–I Tax–Transformed Tumors in Mice by Antisense Inhibition of NF–κB", Science 258:1792–1795 (1992).

Lewis and Mueller, "Intrathecal Baclofen For Severe Spasticity Secondary to Spinal Cord Injury", The Annals of Pharmacotherapy 27:767–774 (1993).

Luer and Hatton, "Vancomycin Administration into the Cerebrospinal Fluid: A Review", The Annals of Pharmacotherapy 27:912–921 (1993).

Chautier–Harlin et al., "Early–onset Alzheimer's disease caused by mutations at codon 717 of the β–amyloid precursor protein gene", Nature 353:844–846 (1991).

Mullan et al., "A pathogenic mutation for probable Alzheimer's disease in the APP gene at the N–terminus of β–amyloid", Nature Genetics 1:345–347 (1992).

Murrell et al., "A Mutation in the Amyloid Precursor Protein Associated with Hereditary Alzheimer's Disease", Science 254:97–99 (1991).

(List continued on next page.)

*Primary Examiner*—Eggerton A. Campbell
*Attorney, Agent, or Firm*—Woodcock Washburn Kurtz Mackiewicz & Norris, LLP

[57] ABSTRACT

Compositions and methods are provided for the modulation of abnormal expression of β-amyloid. Oligonucleotides are provided which are specifically hybridizable with RNA or DNA encoding β-amyloid. Oligonucleotides specifically hybridizable with a translation initiation site, codon 717, codon 670 or codon 671 of βAPP are provided. Such oligonucleotides can be used for diagnostics as well as for research purposes. Methods are also disclosed for modulating β-amyloid expression in cells and tissues using the oligonucleotides provided, and for specific modulation of expression of the mutant βAPP gene. Methods for diagnosis, detection and treatment of diseases associated with abnormal βAPP expression are also disclosed.

3 Claims, No Drawings

OTHER PUBLICATIONS

Nielsen et al., "Sequence–Selective Recognition of DNA of Strand Displacement with a Thymine–Substituted Polyamide", Science 254:1497–1500 (1991).

Offensperger et al., "In vivo inhibition of such hepatitis B virus replication and gene expression by phosphorothioate modified antisense oligodeoxynucleotides", EMBO J. 12:1257–1262 (1993).

Roberts et al., "β Amyloid protein deposition in the brain after severe head injury: implications for the pathogenesis of Alzheimer's disease", J. Neurol. Neurosurg.Psychiatry 57:419–425 (1994).

Roos and Haan, "Function of amyloid and amyloid protein precursor", Clinical Neurology and Neurosurgery 94:–S1–S3 (Supplemental) (1992).

Sambrook et al., "Molecular Cloning. A Laboratory Manual", Cold Spring Harbor Laboratory Press, vol. 2, pp. 10.59 and 11.31–11.32 (1989).

Sarkozi et al., "β–amyloid precursor protein mRNA is increased in inclusion–body myositis muscle", NeuroReport 4:815–818 (1993).

Selkoe, D.J., "Amyloid Protein and Alzheimer's Disease", Scientific American 68–78 (1991).

Simons et al., "Antisense c–myb oligonucleotides inhibit intimal arterial smooth muscle cell accumulation in vivo", Nature 359:67–70 (1992).

Suzuki et al., "An Increased Percentage of Long Amyloid β Protein Secreted by Familial Amyloid β Protein Precursor ($\beta APP_{717}$) Mutants", Science 264:1336–1340 (year ?).

Zimm et al., "Cerebrospinal Fluid Pharmacokinetics of Intraventricular and Intravenous Aziridinyl–benzoquinone", Cancer Research 44:1698–1701 (1984).

This Week in Science, Science 243:1415 (1984).

Whitson et al., "Amyloid β Protein Enhances the Survival of Hippocampal Neurons in vitro", Science 243:1488–1490 (1989).

Chartier–Harlin et al. "Screening for the β–Amyloid Precursor Protein Mutation (APP717: Val–Ile) in Extended Pedigrees with Early Onset Alzheimer's Disease", Neuroscience Letters 129:134–135 (1991).

Nucleic Acids and Molecular Biology, vol. 1, (Springer–Verlag, Berlin), Houba–Herin et al., "Antisense RNA" 210–220 (1987).

Ratner, "Can the Antisense Message Be Delivered" Biotechnology 7:207 (1989).

Dagle et al., "Targeted degradation of mRNA in Xenopus oocytes and embyros directed by modified oligonucleotides: studies of An2 and cyclin in embyrogenesis", Nucleic Acids Research 18:4751–4757 (1990).

Dagle et al., "Pathways of Degradation and Mechanism of Action of Antisense Oligonucleotides in Xenopus laevis Embryos", Antisense Research and Development 1:11–20 (1991).

Dagle et al., "Physical properties of oligonucleotides containing phosphoramidate–modified internucleoside linkages", Nucleic Acids Research 19:1805–1810 (1991).

Eder, P.S. and Walder, J.A., "Ribonuclease H from K562 Human Erythroleukemia Cells", The Journal of Biological Chemistry 266(10):6472–6479 (1991).

Etcheberrigaray et al., "Science β–Amyloid Induction of Alzheimer's Phenotype for Human Fibroblast $K^+$ Channels" Science 264:276–279 (1994).

Marx, "News & Comment: Major Setback for Alzheimer's Models" Science 255:1200–1202 (1992).

Marx, "Boring in on β–Amyloid's Role in Alzheimer's" Science 255:688–689 (1992).

Robakis et al, "Molecular Cloning and Characterization of a cDNA Encoding the Cerebrovascular and the Neuritic Plaque Amyloid Peptides" PNAS USA 84:4190–4194 (1987).

Bioworld Today, Dec. 20, 1993.

Miller and T'so, Anti Cancer Drug Design 2: 117–128, 1987.

Gura, Science 270; 575–577, 1995.

James,Antiviral Chemistry and Chemotherapy 2: 191–214, 1991.

Maury et al. FEBS 276: 75–77, 1990.

Hiltunen et al. Am J. of Hum Genet 49: 522–528, 1991.

Pennis, Science 145: 8–10, 1994.

Bush et al. in Alzheimer's Disease, Amyloid Precursor Proteins, Signal Transduction and Neuronal Transplantation, in Annals of the New York Academy of Sciences, eds Nitsch et al, Published by the New York Academy of Sciences, vol. 695, pp. 175–176, 1993.

Iqbal et al. In Prog. Clin. Biol. Res. 317:679–687, 1989.

Mattson and Rydel, Neurobiology of Aging 13: 617–621, 1992.

Roush, Science 267: 793–794, 1995.

Robakis et al. PNAS 84:4190–4194, 1987.

Goate et al. Nature 349: 704–708, 1991.

Chartier–Harlin, Nature 353: 844–846, 1991.

Almeida et al. Hum. Genetics 85: 623–626, 1990.

Mirra et al. Neurology 41:479–486 (of interest), 1991.

SEQUENCE LISTING ( 1 ) GENERAL INFORMATION:

( i i i ) NUMBER OF SEQUENCES: 53

( 2 ) INFORMATION FOR SEQ ID NO: 1:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 1:

GCCAAACCGG GCAGCATCGC 20

( 2 ) INFORMATION FOR SEQ ID NO: 2:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 2:

AGCATCGCGA CCCTGCGCGG 20

( 2 ) INFORMATION FOR SEQ ID NO: 3:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 3:

AAACCGGGCA GCATCGCGAC 20

( 2 ) INFORMATION FOR SEQ ID NO: 4:

( i ) SEQUENCE CHARACTERISTICS:
( A ) LENGTH: 15
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 4:

GTGATGATGA TCACT 15

( 2 ) INFORMATION FOR SEQ ID NO: 5:

( i ) SEQUENCE CHARACTERISTICS:
( A ) LENGTH: 17
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 5:

GGTGATGATG ATCACTG 17

(2) INFORMATION FOR SEQ ID NO: 6:

(i) SEQUENCE CHARACTERISTICS:
        (A) LENGTH: 19
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 6:

AGGTGATGAT GATCACTGT 19

(2) INFORMATION FOR SEQ ID NO: 7:

(i) SEQUENCE CHARACTERISTICS:
        (A) LENGTH: 21
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 7:

AAGGTGATGA TGATCACTGT C 21

(2) INFORMATION FOR SEQ ID NO: 8:

(i) SEQUENCE CHARACTERISTICS:
        (A) LENGTH: 15
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 8:

GTGATGAAGA TCACT 15

(2) INFORMATION FOR SEQ ID NO: 9:

(i) SEQUENCE CHARACTERISTICS:
        (A) LENGTH: 17
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 9:

GGTGATGAAG ATCACTG 17

(2) INFORMATION FOR SEQ ID NO: 10:

(i) SEQUENCE CHARACTERISTICS:
        (A) LENGTH: 19
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 10:

AGGTGATGAA GATCACTGT 19

(2) INFORMATION FOR SEQ ID NO: 11:

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 11:

AAGGTGATGA AGATCACTGT C                             21

( 2 ) INFORMATION FOR SEQ ID NO: 12:

( i ) SEQUENCE CHARACTERISTICS:
  ( A ) LENGTH: 15
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 12:

GTGATGCCGA TCACT                                    15

( 2 ) INFORMATION FOR SEQ ID NO: 13:

( i ) SEQUENCE CHARACTERISTICS:
  ( A ) LENGTH: 17
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 13:

GGTGATGCCG ATCACTG                                  17

( 2 ) INFORMATION FOR SEQ ID NO: 14:

( i ) SEQUENCE CHARACTERISTICS:
  ( A ) LENGTH: 19
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 14:

AGGTGATGCC GATCACTGT                                19

( 2 ) INFORMATION FOR SEQ ID NO: 15:

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 15:

AAGGTGATGC CGATCACTGT C                             21

( 2 ) INFORMATION FOR SEQ ID NO: 16:

( i ) SEQUENCE CHARACTERISTICS:
  ( A ) LENGTH: 15
  ( B ) TYPE: nucleic acid
  ( C ) STRANDEDNESS: single
  ( D ) TOPOLOGY: linear (i v) ANTI-SENSE: yes (x i) SEQUENCE DESCRIPTION: SEQ ID NO: 16:

GTGATGACGA TCACT                                                                 15

(2) INFORMATION FOR SEQ ID NO: 17:

(i) SEQUENCE CHARACTERISTICS:
        (A) LENGTH: 17
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 17:

GGTGATGACG ATCACTG                                                               17

(2) INFORMATION FOR SEQ ID NO: 18:

(i) SEQUENCE CHARACTERISTICS:
        (A) LENGTH: 19
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 18:

AGGTGATGAC GATCACTGT                                                             19

(2) INFORMATION FOR SEQ ID NO: 19:

(i) SEQUENCE CHARACTERISTICS:
        (A) LENGTH: 21
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 19:

AAGGTGATGA CGATCACTGT C                                                          21

(2) INFORMATION FOR SEQ ID NO: 20:

(i) SEQUENCE CHARACTERISTICS:
        (A) LENGTH: 15
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 20:

GTGATGNNGA TCACT                                                                 15

(2) INFORMATION FOR SEQ ID NO: 21:

(i) SEQUENCE CHARACTERISTICS:
        (A) LENGTH: 17
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 21:

GGTGATGNNG ATCACTG                                                                                17

( 2 ) INFORMATION FOR SEQ ID NO: 22:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 22:

AGGTGATGNN GATCACTGT                                                                              19

( 2 ) INFORMATION FOR SEQ ID NO: 23:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 23:

AAGGTGATGN NGATCACTGT C                                                                           21

( 2 ) INFORMATION FOR SEQ ID NO: 24:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 24:

ACATTATGCT AGCGCAGCGG TAGGCGAGAG CAC                                                               33

( 2 ) INFORMATION FOR SEQ ID NO: 25:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 25:

GAGATCTGAA GCTTCGTCCA GGCGGCCAGC AGGA                                                              34

( 2 ) INFORMATION FOR SEQ ID NO: 26:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 26:

GAGATCTGAA GCTTGGTGCA ATCATTGGAC TCATG                                                             35

( 2 ) INFORMATION FOR SEQ ID NO: 27:

( i ) SEQUENCE CHARACTERISTICS:
  ( A ) LENGTH: 44
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 27:

GAGATCTGAA GCTTACCACC CCTCAGCATC ACCAAGGTGA TGAC　　　　44

( 2 ) INFORMATION FOR SEQ ID NO: 28:

( i ) SEQUENCE CHARACTERISTICS:
    ( A ) LENGTH: 15
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 28:

GCATCCAGAT TCACT　　　　15

( 2 ) INFORMATION FOR SEQ ID NO: 29:

( i ) SEQUENCE CHARACTERISTICS:
    ( A ) LENGTH: 15
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 29:

CATCCAGATT CACTT　　　　15

( 2 ) INFORMATION FOR SEQ ID NO: 30:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 30:

TGCATCCAGA TTCACTT　　　　17

( 2 ) INFORMATION FOR SEQ ID NO: 31:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 31:

GCATCCAGAT TCACTTC　　　　17

( 2 ) INFORMATION FOR SEQ ID NO: 32:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 32:

CTGCATCCAG ATTCACTTC 19

( 2 ) INFORMATION FOR SEQ ID NO: 33:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 33:

TGCATCCAGA TTCACTTCA 19

( 2 ) INFORMATION FOR SEQ ID NO: 34:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 34:

TCTGCATCCA GATTCACTTC A 21

( 2 ) INFORMATION FOR SEQ ID NO: 35:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 35:

CTGCATCCAG ATTCACTTCA G 21

( 2 ) INFORMATION FOR SEQ ID NO: 36:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 36:

CATCCATCTT CACTT 15

( 2 ) INFORMATION FOR SEQ ID NO: 37:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 37:

GCATCCATCT TCACT                                                    15

( 2 ) INFORMATION FOR SEQ ID NO: 38:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 38:

GCATCCATCT TCACTTC                                                  17

( 2 ) INFORMATION FOR SEQ ID NO: 39:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 39:

TGCATCCATC TTCACTT                                                  17

( 2 ) INFORMATION FOR SEQ ID NO: 40:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 40:

TGCATCCATC TTCACTTCA                                                19

( 2 ) INFORMATION FOR SEQ ID NO: 41:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 41:

CTGCATCCAT CTTCACTTA                                                19

( 2 ) INFORMATION FOR SEQ ID NO: 42:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 42:

CTGCATCCAT CTTCACTTCA G                                             21

( 2 ) INFORMATION FOR SEQ ID NO: 43:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 43:

TCTGCATCCA TCTTCACTTC A                         21

( 2 ) INFORMATION FOR SEQ ID NO: 44:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 44:

CATCCANNTT CACTT                              15

( 2 ) INFORMATION FOR SEQ ID NO: 45:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 45:

GCATCCANNT TCACT                              15

( 2 ) INFORMATION FOR SEQ ID NO: 46:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 46:

GCATCCANNT TCACTTC                            17

( 2 ) INFORMATION FOR SEQ ID NO: 47:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 47:

TGCATCCANN TTCACTT                            17

( 2 ) INFORMATION FOR SEQ ID NO: 48:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear (i v) ANTI-SENSE: yes (x i) SEQUENCE DESCRIPTION: SEQ ID NO: 48:

TGCATCCANN TTCACTTCA                                                                19

(2) INFORMATION FOR SEQ ID NO: 49:

(i) SEQUENCE CHARACTERISTICS:
                (A) LENGTH: 19
                (B) TYPE: nucleic acid
                (C) STRANDEDNESS: single
                (D) TOPOLOGY: linear (i v) ANTI-SENSE: yes (x i) SEQUENCE DESCRIPTION: SEQ ID NO: 49:

CTGCATCCAN NTTCACTTC                                                                19

(2) INFORMATION FOR SEQ ID NO: 50:

(i) SEQUENCE CHARACTERISTICS:
                (A) LENGTH: 21
                (B) TYPE: nucleic acid
                (C) STRANDEDNESS: single
                (D) TOPOLOGY: linear (i v) ANTI-SENSE: yes (x i) SEQUENCE DESCRIPTION: SEQ ID NO: 50:

CTGCATCCAN NTTCACTTCA G                                                             21

(2) INFORMATION FOR SEQ ID NO: 51:

(i) SEQUENCE CHARACTERISTICS:
                (A) LENGTH: 21
                (B) TYPE: nucleic acid
                (C) STRANDEDNESS: single
                (D) TOPOLOGY: linear (i v) ANTI-SENSE: yes (x i) SEQUENCE DESCRIPTION: SEQ ID NO: 51:

TCTGCATCCA NNTTCACTTC A                                                             21

(2) INFORMATION FOR SEQ ID NO: 52:

(i) SEQUENCE CHARACTERISTICS:
                (A) LENGTH: 26
                (B) TYPE: nucleic acid
                (C) STRANDEDNESS: single
                (D) TOPOLOGY: linear (x i) SEQUENCE DESCRIPTION: SEQ ID NO: 52:

GTCATAGCGA CAGTGATCGT CATCAC                                                        26

(2) INFORMATION FOR SEQ ID NO: 53:

(i) SEQUENCE CHARACTERISTICS:
                (A) LENGTH: 8
                (B) TYPE: amino acid
                (C) STRANDEDNESS:
                (D) TOPOLOGY: unknown (x i) SEQUENCE DESCRIPTION: SEQ ID NO: 53:

Val Ile Ala Thr Val Ile Val Ile
 1               5

COMPOSITIONS AND METHODS FOR MODULATING β-AMYLOID

This application is a Continuation-In-Part of U.S. patent application Ser. No. 07/814,963, filed Dec. 24, 1991 now abandoned.

FIELD OF THE INVENTION

This invention relates to the design and synthesis of oligonucleotides that are complementary to and specifically hybridizable with nucleic acids encoding β-amyloid protein. The oligonucleotides of the invention are useful in assays for β-amyloid and as diagnostic reagents for the detection of diseases associated with abnormal accumulation of β-amyloid. The oligonucleotides of this invention may also be used either prophylactically or therapeutically to reduce the severity of disease states resulting from abnormal accumulation of β-amyloid in the cells and tissues of a human patient.

BACKGROUND OF THE INVENTION

Abnormal deposition of β-amyloid in the cells and tissues of a human patient is a prominent feature associated with several brain disorders in humans. These disorders include Alzheimer's disease, Alzheimer disease changes associated with Down's syndrome, hereditary cerebral hemorrhage with amyloidosis of Dutch origin (HCHWA-D), Parkinson-dementia of Guam, sporadic cerebral amyloid angiopathy (SCAA) and dementia pugilistica. Abnormal accumulation of β-amyloid is also implicated in severe and progressive muscle diseases such as sporadic inclusion body myositis (IBM) and hereditary inclusion body myopathy (hIBM). Collectively, these diseases are referred to as β-amyloidoses.

Alzheimer's disease is the most common cause of dementia in aging humans in many developed countries. The disease is characterized by gradual loss of memory, emotional stability and judgment. Death usually occurs between four and twelve years after the onset of symptoms. Patients with Alzheimer's disease require constant supervision and eventual total custodial care due to their severely debilitated condition. The cost of diagnosing and managing Alzheimer's patients is currently estimated at more than $80 billion a year in the U.S. alone [Selkoe, D. J. (1991) *Scientific American* 265:68–78].

Two types of brain lesions, senile plaques and neurofibrillary tangles, were originally described by Dr. Alois Alzheimer in patients with dementia. In Alzheimer's disease patients, senile plaques occur in great numbers in the areas of the brain responsible for cognitive function, particularly the cerebral cortex, hippocampus and amygdala. These spherical plaques consist of altered neurites (axons and dendrites), which are the long tapering portions of neurons, surrounding an extracellular mass of filaments. It is presently believed that degeneration of neurons in Alzheimer's disease patients is the result of their entanglement in this filament matrix. There is currently no treatment for the prevention or retardation of the progression of Alzheimer's disease.

At approximately 40–50 years of age, individuals with Down's syndrome acquire brain lesions which are characteristic of Alzheimer's disease. The behavior as well as the mental ability of these patients begins to deteriorate at about the same time. The cerebrovascular plaques which are observed in Down's syndrome patients over forty years of age are known to comprise β-amyloid. Also, recent studies suggest that women under age 35 who have borne a child with Down's syndrome are themselves more likely to develop Alzheimer's disease earlier in life than women who bear children with Down's syndrome at or above age 35.

Hereditary cerebral hemorrhage with amyloidosis of Dutch type (HCHWA-D) is an autosomal dominant disease characterized by extensive β-amyloid plaques in the cerebral cortex. The senile plaques are widespread and have a fibrillar appearance. Also, amyloid fibrils are known to infiltrate small arteries, arterioles and veins in these individuals. Patients with HCHWA-D suffer recurrent intracerebral hemorrhages leading to early death at the age of 50 to 60 years old. In almost 50% of the patients the first cerebral hemorrhage leads to death.

Parkinson-dementia of Guam is caused by extensive deposition of β-amyloid in the brain, and is characterized by parkinsonism and slowly progressive dementia. This disease also exhibits the formation of neurofibrillary tangles similar to those observed in Alzheimer's disease patients.

Sporadic cerebral amyloid angiopathy (SCAA) is characterized by an intense and extensive β-amyloid deposition within cerebral arteries, veins, arterioles and capillaries. SCAA is observed in 50% of the autopsies performed on individuals over 50 years of age. Symptoms include dementia, cerebral hemorrhages and ischemic strokes.

Severe head injury in humans may lead to a chronic degenerative condition referred to as dementia pugilistica. This disorder is a consequence of abnormal deposition of β-amyloid in the form of diffuse plaques in the neurons and neurites of the patient's brain, and is characterized by a cavum septum, neuronal loss, cerebellar scarring and intense neurofibrillary tangle formation in the cortex.

Muscle diseases such as sporadic inclusion body myositis (IBM) and hereditary inclusion body myopathy (hIBM) are characterized by abnormal accumulation of β-amyloid in vacuolated muscle fibers, and are most common in patients of who are fifty-five years of age or older. This is a progressive disease resulting in severe disability, whose symptoms include proximal and distal muscle weakness, thinning of the forearms, male predominance and either the absence of or a poor response to immunosuppressive treatment.

There is a long felt need for effective diagnosis, prophylaxis and treatment of these and other conditions whose common feature includes abnormal β-amyloid synthesis and accumulation.

SUMMARY OF THE INVENTION

β-Amyloid is a small protein approximately 40 amino acids in length, which is derived from the carboxyl terminus of a much longer (770 amino acids) precursor protein called β-amyloid precursor protein (βAPP). The gene which encodes βAPP therefore also encodes β-amyloid.

In accordance with the present invention, oligonucleotides are provided that are specifically hybridizable with DNA or RNA encoding abnormally expressed β-amyloid. The oligonucleotides comprise nucleotide units sufficient in identity and number to effect such specific hybridization. Abnormally expressed β-amyloid includes overexpressed β-amyloid, β-amyloid with reduced solubility, β-amyloid which is longer than wild type β-amyloid, preferably comprising at least 42 amino acid residues, and mutated β-amyloid. In accordance with another preferred embodiment, oligonucleotides that specifically hybridize with codon 717 of the gene encoding β-amyloid are provided. In another such embodiment, oligonucleotides are provided that specifically hybridize preferentially with codon 717 of the gene encoding a mutated β-amyloid, preferably comprising a sequence GAT, GAA or GCC. In yet another embodiment, oligonucleotides that specifically hybridize with codons 670 and 671 of the gene encoding β-amyloid are provided. In another such embodiment, oligonucleotides are provided that specifically hybridize preferentially with codons 670 and 671 of the gene encoding a mutated β-amyloid. Such oligonucleotides may be conveniently and desirably presented in a pharmaceutically acceptable carrier.

In accordance with other preferred embodiments, the oligonucleotides are formulated such that at least one of the linking groups between nucleotide units of the oligonucleotide comprises a sulfur-containing species such as a phosphorothioate moiety.

Other aspects of the invention are directed to methods for modulating the expression of β-amyloid in cells or tissues and for specifically modulating the expression of mutated β-amyloid in cells or tissues suspected of harboring such a mutation. Additional aspects of the invention are directed to methods of detecting the gene encoding β-amyloid in cells or tissues and specific detection of the gene encoding mutated β-amyloid in cells or tissues suspected of harboring the mutated gene. Such methods comprise contacting cells, tissues or bodily fluids suspected of containing the gene with oligonucleotides in accordance with the invention in order to interfere with the effect of or to detect the gene.

Other aspects of the invention are directed to methods for diagnostics and therapeutics of animals suspected of having a mutation in the gene encoding β-amyloid. Such methods comprise contacting the animal or cells or tissues or a bodily fluid from the animal with oligonucleotides in accordance with the invention in order to modulate the expression of this gene, to treat conditions arising from abnormal expression, overexpression or mutation of this gene, or to effect a diagnosis thereof.

DETAILED DESCRIPTION OF THE INVENTION

In accordance with the present invention, oligonucleotides that modulate the expression of β-amyloid are provided. These oligonucleotides are useful in assays for β-amyloid, as diagnostics for the detection of β-amyloid, and for specific modulation of expression of β-amyloid, and particularly for specific modulation of expression of mutant forms of β-AMYLOID which leads to β-amyloidoses, which is characterized by deposition of β-amyloid plaques in cells and tissues of animals and man.

The principal constituent of the extracellular filaments which form the center of amyloid plaques is not starch, as the name suggests, but protein. The identity of the amyloid proteins found in these filaments differs among the various diseases, termed amyloidoses, which are characterized by deposits of wild type or mutated amyloid protein. Amyloid which was originally isolated from blood vessels in the meninges of patients with Alzheimer's disease, comprises a small protein, named the β-protein. Isolated amyloid cores of senile plaques obtained from the brains of Alzheimer's disease patients were subsequently found to comprise the same β-protein. The gene encoding βAPP and β-amyloid is located on human chromosome 21; this location is believed to account for the development of β-amyloid deposits and the early onset of symptoms of Alzheimer's disease in Down syndrome patients due to the fact that they contain an extra copy of this chromosome [Selkoe, D. J. (1991) Scientific American, 265:68–78].

The distinction between normal aging and Alzheimer's disease at the pathological level is largely quantitative rather than qualitative. Most people develop some neurofibrillary tangles and senile plaques by the age of 70 or 80 years. However, the number of mature plaques and tangles is greater, sometimes by very large amounts, in patients with Alzheimer's disease compared with age-matched controls. Diffuse pre-amyloid plaques arise in the brain tissue of Alzheimer's disease patients which are frequently more abundant than mature neuritic plaques. Using highly sensitive molecular probes, such diffuse plaques have been detected, not only in the cerebral cortex (the area of the brain involved in cognitive function and implicated in symptoms of dementia) but also in other regions of the brain. Patients with Down's syndrome who die prior to reaching adulthood (i.e., as teenagers), before the inevitable Alzheimer's symptoms appear, have many such diffuse plaques. The onset of β-amyloid deposition therefore precedes the development of mature plaques with neuron involvement. The abnormal accumulation of β-amyloid is therefore believed to be the cause, rather than a symptom, of Alzheimer's disease. This accumulation may occur through a number of genetic mechanisms.

β-Amyloid deposits have also been found in and around blood vessels of the meninges, skin, intestine and other tissues of Alzheimer's disease patients. The process underlying β-amyloid deposition is therefore not restricted to the brain. The propensity of these deposits to arise in close proximity to blood vessels suggests that Alzheimer's disease may be similar in character to some systemic amyloidoses which are known to have a circulatory origin. Localization of β-amyloid in epithelial cells of the blood vessel walls suggests that the β-amyloid protein which accumulates in the brain may originate in the bloodstream [Selkoe, D. J. (1991) Scientific American, 265:68–78]. Systemic treatment of patients with such deposits may therefore be possible. In addition, direct administration of compounds into the central nervous system (CNS) is also possible using accepted treatment modalities such as intrathecal drug administration [Lewis and Mueller (1993) The Annals of Pharmacotherapy 27:767–774; Luer and Hatton (1993) The Annals of Pharmacotherapy 27:912–921].

The results of research conducted on families afflicted with a hereditary form of Alzheimer's disease, known as familial Alzheimer's disease (FAD), has established that in some families, all members with Alzheimer's disease exhibit a mutation in codon 717 of the βAPP gene, which codon is contained within the β-amyloid peptide region. [In a separate numbering system, codon 717 (out of a total of 770 codons) may be referred to as codon 642 (out of a total of 695 codons)]. Strikingly, while these mutations are not identical at the DNA level, each mutation comprises a single-base change which effects replacement of valine, the wild type amino acid normally encoded by codon 717, with another amino acid such as isoleucine, phenylalanine, or glycine [Goate et al. (1991) Nature 349:704–706; Murrell et al. (1991) Science 254:97–99; Chartier-Harlin et al. (1991) Nature 353:844–846]. The specific DNA mutations discovered in patients with FAD and the corresponding amino acid changes are presented in Table 1.

TABLE 1

MUTATIONS AT CODON 717 IN FAMILIAL ALZHEIMER'S DISEASE

| Normal: | GTC | ATA | GCG | ACA | GTG | ATC | GTC | ATC | AC (SEQ ID NO:52) |
|---|---|---|---|---|---|---|---|---|---|
|  | val | ile | ala | thr | val | ile | val | ile | ... (SEQ ID NO:53) |
| Mutations found in Familial Alzheimer's Disease (FAD) | ... | ... | ... | ... | ... | ... | ATC | ... | ... |
|  | ... | ... | ... | ... | ... | ... | ile | ... | ... |
|  | ... | ... | ... | ... | ... | ... | TTC | ... | ... |
|  | ... | ... | ... | ... | ... | ... | phe | ... | ... |
|  | ... | ... | ... | ... | ... | ... | GGC | ... | ... |
|  | ... | ... | ... | ... | ... | ... | gly | ... | ... |

The tight correlation between mutations in codon 717 and Alzheimer's disease patients in FAD families, and the fact that such mutations have not otherwise been found to occur in non-Alzheimer's individuals, suggests that these mutations in fact cause the overaccumulation of β-amyloid and thus the disease.

In addition to overaccumulation of β-amyloid, mutation of codon 717 results in the appearance of an increased percentage of β-amyloid comprising at least 42 amino acid residues which is referred to as long β-amyloid (in contrast to the normal 40-amino acid form). Long β-amyloid is marginally soluble in aqueous solution at physiological pH and forms deposits in tissues, which deposits are implicated as causative agents of diseases related to β-amyloidoses [Suzuki et al. (1994) *Science* 264:1336–1340; Burdick et al. (1992) *The Journal of Biological Chemistry* 267:546–554].

It is currently believed that in addition to mutation of codon 717, a separate set of mutations in the βAPP gene is also involved in the development of β-amyloidoses. Double mutation of the βAPP gene at codons 670 and 671 predicts lysine-to-asparagine and methionine-to-leucine amino acid substitutions, respectively. [In a separate numbering system, codons 670 and 671 (out of a total of 770) are frequently referred to as codons 595 and 596 (out of a total of 695)]. Cells whose DNA has this double mutation have been shown to produce markedly greater amounts of β-amyloid compared with cells encoding the wild type form of the protein [Cai et al. (1993) *Science* 259:514–516], which increase may be as high as 6 to 8-fold and is associated with a particular form of FAD [Citron et al. (1992) *Nature* 360:672–674]. Abnormal accumulation and deposition of β-amyloid as well as increased expression of long β-amyloid are the direct result of mutation of the βAPP gene.

There is a body of literature demonstrating the ability of oligonucleotides to penetrate cells and illicit therapeutic response. Offensperger et al. [*EMBO J.* 12 1257–1262 (1993)] disclose a phosphorothioate-modified antisense oligonucleotide directed against duck hepatitis B virus. When administered intravenously to ducks, the oligonucleotide resulted in complete inhibition of virus replication and viral gene expression. Inhibition of virus replication in ducks demonstrated clear correlation with in vitro studies performed in primary duck hepatocytes. No toxicity was evident in either infected or uninfected ducks when treated with the oligonucleotide. These results clearly establish that intravenous administration of antisense oligonucleotides results in cell penetration and is a viable therapeutic modality for the treatment of viral infections.

Simons et al. [*Nature* 359 67–70 (1992)] discuss a phosphorothioate-modified c-myb antisense oligonucleotide that is effective as a suppressor of smooth muscle cell proliferation, both in vitro in smooth muscle cells in culture and in vivo in the carotid artery of rats. The data presented demonstrate efficacy of the oligonucleotide in cell culture and correlation of in vitro efficacy with that observed in vivo.

Burch et al. [*J. Clinical Investig.* 88 1190–1196 (1991)], Kitajima et al. [*Science* 258 1792–1795 (1992)], and Higgins et al. [*Proc. Natl. Acad. Sci. USA* 90 9901–9905 (1993)] disclose antisense oligonucleotides that exhibit in vivo efficacy upon subcutaneous or intraperitoneal injection in mice, and in vitro effectiveness in cell culture. These data also demonstrate that the efficacy of the oligonucleotides in vitro correlates well with that observed in vivo.

Determination of the activity of oligonucleotides in vitro is now accepted as a basis for predictions regarding their in vivo efficacy for the treatment of diseases for which they are designed.

Antisense oligonucleotides have been safely administered to humans and several clinical trials are presently underway. Based on these clinical trials, oligonucleotides are understood to have toxicities within acceptable limits at dosages required for therapeutic efficacy. One such antisense oligonucleotide, identified as ISIS 2105, is presently in clinical trials, and is used as a therapeutic against papillomavirus. Another antisense oligonucleotide, ISIS 2922, has been shown to have clinical efficacy against cytomegalovirus-associated retinitis [*Antiviral Agents Bulletin* 5 161–163 (1992); *BioWorld Today*, Dec. 20, 1993]. It has, therefore, been established that oligonucleotides are useful therapeutic instrumentalities and that the same can be configured to be useful in regimes for treatment of animals, especially humans.

Oligonucleotides have recently become accepted as therapeutic moieties in the treatment of disease states in animals and man. For example, U.S. Pat. No. 5,098,890 is directed to antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence with a portion of an oncogene. U.S. Pat. Nos. 5,276,019 and 5,264,423 are directed to oligonucleotide analogs used to prevent replication of foreign nucleic acids in cells. U.S. Pat. No. 4,689,320 is directed to antisense oligonucleotides as antiviral agents specific to CMV. U.S. Pat. No. 4,999,421 is directed to peptides expressed by the antisense strand of HTLV-1. U.S.

Pat. No. 5,242,906 provides antisense oligonucleotides useful in the treatment of latent EBV infections.

The present invention employs oligonucleotides specifically hybridizable to nucleic acids encoding βAPP. This relationship between an oligonucleotide and the complementary nucleic acid target to which it hybridizes is commonly referred to asZ "antisense." "Targeting" an oligonucleotide to a chosen nucleic acid target, in the context of this invention, so that the oligonucleotide is specifically hybridizable with the target, is a multistep process. The process usually begins by identifying a nucleic acid sequence whose function is to be modulated. This nucleic acid may be, by way of example, a cellular gene (or an RNA specified by that cellular gene) whose expression is associated with a particular disease state, or it may be a nucleic acid obtained from an infectious agent. In the present invention, the target is a nucleic acid encoding β-amyloid; in other words, the β-amyloid gene or RNA specified by the β-amyloid gene. The targeting process also includes determination of a site or sites within the nucleic acid sequence for the oligonucleotide interaction to occur such that the desired effect, namely, modulation of gene expression, will result. Once the target site or sites have been identified, oligonucleotides are chosen which are sufficiently complementary to the target, i.e., hybridize sufficiently well and with sufficient specificity, to give the desired modulation, or in the case of probes and diagnostics, the desired binding.

In the context of this invention, "modulation" means either inhibition or stimulation of gene expression. Inhibition of abnormal β-amyloid gene expression is presently the preferred form of modulation. This modulation can be measured in ways which are routine in the art and which are described in any ordinary molecular biology manual such as Sambrook et al. [*Molecular Cloning: A Laboratory Manual*, Cold Spring Harbor Laboratory Press, NY (1989)]. For example, assessment of RNA expression may be accomplished using Northern blot or slot blot hybridization assays, primer extension and poly A+ assays etc. Similarly, assays to detect expression of protein include Western blot assays, radioimmunoassays and enzyme linked immunoabsorbent assays and the like. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which pair with each other through the formation of three hydrogen bonds. Adenine and thymine are also examples of complementary bases which pair through the formation of two hydrogen bonds.

"Complementary," as used herein, also refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, "specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms in that they may exhibit enhanced cellular uptake, increased stability in the presence of nucleases, and other features which render them more acceptable as therapeutic or diagnostic reagents.

The present invention includes oligonucleotides specifically hybridizable to nucleic acids encoding βAPP. In preferred embodiments, the oligonucleotides are specifically hybridizable with an mRNA encoding βAPP. More preferably, oligonucleotides may be formulated in accordance with this invention which are specifically hybridizable either wholly or in part to the translation initiation site, codon 717, codon 670 or codon 671 of the mRNA encoding βAPP. These oligonucleotides are useful in detection and diagnostics, and for modulating βAPP expression by interfering with βAPP RNA function. The functions of the RNA to be interfered with through such hybridization include essential functions such as transport of the RNA within the cell, mRNA translation, including initiation, elongation and termination, splicing or maturation of the RNA and even independent catalytic activity of the mRNA. The overall effect of such interference with RNA function is to modulate expression of βAPP using the oligonucleotides of the invention.

Specific examples of preferred oligonucleotides included in the invention contain phosphorothioate, phosphotriester, methyl phosphonate, short chain alkyl or cycloalkyl intersugar linkages, or short chain heteroatomic or heterocyclic intersugar ("backbone") linkages. Most preferred are phosphorothioate oligonucleotides and oligonucleotides comprising $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$) 13 $CH_2$—$CH_2$ backbones (wherein phosphodiester is O—P—O—$CH_2$). Also preferred are oligonucleotides having morpholino backbone structures [Summerton, J. E. and Weller, D. D., U.S. Pat. No. No: 5,034,506].

In other preferred embodiments, oligonucleotides are designed to contain a protein-nucleic acid or peptide-nucleic acid (PNA) backbone, wherein the phosphodiester backbone of the oligonucleotide is replaced with a polyamide backbone, the bases being bound directly or indirectly to the aza nitrogen atoms of the polyamide backbone [P. E. Nielsen et al. (1991) *Science* 254:1497]. Yet other preferred oligonucleotides may contain alkyl and halogen-substituted sugar moieties comprising one of the following moieties at the 2' position: OH, SH, $SCH_3$, F, OCN, $OCH_2OCH_3$, $OCH_2O(CH_2)_nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine.

The invention may also include oligonucleotides which are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance of the oligonucleotide to nuclease degradation, increased cellular uptake, and/or increased binding affinity for the target nucleic acid. An additional region of the oligonucleotide may serve as a substrate for cleavage by RNase H or other enzymes capable of cleaving RNA:DNA or RNA:RNA hybrids. RNAse H is a cellular endonuclease which cleaves the RNA strand of a RNA:DNA duplex; activation of this enzyme therefore results in cleavage of the RNA target, thereby greatly enhancing the efficiency of antisense inhibition of gene expression. Cleavage of the RNA target can be routinely demonstrated by gel electrophoresis.

In one preferred embodiment, a chimeric oligonucleotide comprises at least one region which is modified so as to increase the binding affinity of the oligonucleotide to the target nucleic acid. Affinity of an oligonucleotide for its target (in this case a nucleic acid encoding βAPP) is routinely determined by measuring the thermal melting point ($T_m$) of the oligonucleotide/target pair. The $T_m$ is the temperature at which the oligonucleotide and target dissociate from each other, which dissociation is detected spectrophotometrically. The higher the $T_m$, the greater the affinity of the oligonucleotide for the target. In a more preferred embodiment, the region of the oligonucleotide which is modified to increase βAPP RNA binding affinity comprises at least one nucleotide modified at the 2' position of the sugar, most preferably a 2'-O-alkyl or 2'-fluoro-modified nucleotide. Such modifications are routinely incorporated into oligonucleotides and oligonucleotides so modified exhibit a higher $T_m$ (i.e., higher target binding affinity) than their unmodified counterparts when bound to a given target. An increased binding affinity serves frequently to greatly enhance antisense oligonucleotide inhibition of gene expression.

In another preferred embodiment, the chimeric oligonucleotide is also modified to enhance its resistance to nuclease digestion. Cells contain a variety of exo- and endonucleases capable of degrading nucleic acids. A number of nucleotide and nucleoside modifications have been shown to render oligonucleotides into which such modifications are incorporated, more resistant to nuclease digestion than their unmodified counterparts. Nuclease resistance is routinely measured by incubation of oligonucleotides in the presence of a cellular extract or a solution containing nuclease, and measuring any subsequent degradation of the oligonucleotide with time. A variety of oligonucleotide modifications confer enhanced nuclease resistance to oligonucleotides. Oligonucleotides which contain at least one phosphorothioate modification are presently more preferred. In some cases, oligonucleotide modifications which enhance target binding affinity are also, independently, capable of enhancing nuclease resistance.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of a routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other modified oligonucleotides such as cholesterol-modified oligonucleotides.

It has now been found that certain oligonucleotides targeted to portions of the βAPP RNA are particularly useful for inhibiting βAPP expression and for interfering with β-amyloid synthesis. Methods for inhibiting βAPP expression using antisense oligonucleotides are, likewise, useful for interfering with β-amyloid synthesis. In the methods of the invention, tissues or cells are contacted with oligonucleotides. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

For therapeutics, methods of treating a condition arising from abnormal β-amyloid expression are provided. "Abnormal expression," as used herein, refers to overproduction of β-amyloid or production of mutant β-amyloid including, but not limited to, the type referred to as "long" β-amyloid and the hereinbefore described mutant forms of β-amyloid with mutations at codon 717, 670 or 671. The formulation of therapeutic compositions and their subsequent administration is believed to be within the skill of those in the art. In general, for therapeutics, a patient suspected of requiring such therapy is administered an oligonucleotide in accordance with the invention, commonly in a pharmaceutically acceptable carrier, in amounts and for periods of time which will vary depending upon the nature of the particular disease, its severity and the patient's overall condition. The pharmaceutical compositions of this invention may be administered in a number of ways depending upon whether local or systemic treatment is desired, and upon the area to be treated. Administration may be topical (including ophthalmic, vaginal, rectal, intranasal, transdermal), oral or parenteral, for example, by intravenous drip, subcutaneous, intraperitoneal or intramuscular injection or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is LIPOFECTIN (GIBCO-BRL, Bethesda, Md.).

Dosing is dependent on severity and responsiveness of the condition to be treated, with the course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be estimated based on $EC_{50}$'s in in vitro and in vivo animal studies. In general, dosage is from 0.01 µg to 100 g and may be given once daily, weekly, monthly or yearly, or even every 2 to 20 years.

The oligonucleotides of the invention are also useful as diagnostic and prophylactic agents, and as components of research reagents and kits. Since the oligonucleotides of this invention hybridize to the βAPP gene and its mRNA, sandwich and other assays can easily be constructed, using technology which is readily available to those skilled in the art, to exploit this fact. Furthermore, since the oligonucleotides of this invention hybridize preferentially to mutant forms of the βAPP gene, assays can be designed which facilitate screening of cells and tissues for both mutant and wild type forms of βAPP, thereby providing a test which distinguishes between them. Further, this type of test is capable of assessing whether or not the DNA of an individual at risk for Alzheimer's has converted from the wild type to a mutant form of βAPP. Such assays may therefore be used for diagnosis of FAD arising as a result of a mutation in the βAPP gene. Methods for detecting hybridization of an oligonucleotide to βAPP gene sequences can routinely be accomplished by those skilled in the art. Such methods include enzymatic conjugation, radiolabelling and other suitable detection systems. A kit for detecting the presence or absence of the βAPP gene or for detecting mutated βAPP may also be prepared. The kit contains reagents for detecting the presence or absence of βAPP or for detecting mutant forms of βAPP and instructions for using the kit.

The present invention is also suitable for diagnosing diseases caused by abnormal β-amyloid expression in tissue or other samples from patients suspected of having β-amyloidoses. A number of assays may be formulated employing the present invention, which assays will commonly comprise contacting a tissue sample or sample of a bodily fluid with an oligonucleotide specifically hybridizable with wild-type βAPP, and which may be one of the following sequences (set 1):

GTG ATG ACG ATC ACT (SEQ ID NO: 16)

GGT GAT GAC GAT CAC TG (SEQ ID NO: 17)

-continued

AGG TGA TGA CGA TCA CTG T (SEQ ID NO:18) or

AAG GTG ATG ACG ATC ACT GTC (SEQ ID NO: 19),

An identical tissue or bodily fluid sample is then contacted with an oligonucleotide of the invention which may be one of the following (set 2):

5'----------------------------------------------------------------3'

GTG ATG ATG ATC ACT (SEQ ID NO: 4)

GGT GAT GAT GAT CAC TG (SEQ ID NO:5)

AGG TGA TGA TGA TCA CTG T (SEQ ID NO: 6)

AAG GTG ATG ATG ATC ACT GTC (SEQ ID NO: 7)

GTG ATG AAG ATC ACT (SEQ ID NO: 8)

GGT GAT GAA GAT CAC TG (SEQ ID NO: 9)

AGG TGA TGA AGA TCA CTG T (SEQ ID NO: 10)

AAG GTG ATG AAG ATC ACT GTC (SEQ ID NO: 11)

GTG ATG CCG ATC ACT (SEQ ID NO: 12)

GGT GAT GCC GAT CAC TG (SEQ ID NO: 13)

AGG TGA TGC CGA TCA CTG T (SEQ ID NO:14) or

AAG GTG ATG CCG ATC ACT GTC (SEQ ID NO: 15)

under conditions selected to permit detection and quantitation. Alternatively the first oligonucleotide (set 1) may be:

5'-----------------------------------------------------------3'

CAT CCA TCT TCA CTT (SEQ ID NO:36)

GCA TCC ATC TTC ACT (SEQ ID NO:37)

GCA TCC ATC TTC ACT TC (SEQ ID NO:38)

TGC ATC CAT CTT CAC TT (SEQ ID NO:39)

TGC ATC CAT CTT CAC TTC A (SEQ ID NO:40)

CTG CAT CCA TCT TCA CTT C (SEQ ID NO:41)

CTG CAT CCA TCT TCA CTT CAG (SEQ ID NO:42) or

TCT GCA TCC ATC TTC ACT TCA (SEQ ID NO:43), and the second oligonucleotide (set 2) may be:

5'-----------------------------------------------------------3'

GCA TCC AGA TTC ACT (SEQ ID NO:28)

CAT CCA GAT TCA CTT (SEQ ID NO:29)

TGC ATC CAG ATT CAC TT (SEQ ID NO:30)

GCA TCC AGA TTC ACT TC (SEQ ID NO:31)

CTG CAT CCA GAT TCA CTT C (SEQ ID NO:32)

TGC ATC CAG ATT CAC TTC A (SEQ ID NO:33)

TCT GCA TCC AGA TTC ACT TCA (SEQ ID NO:34) or

CTG CAT CCA GAT TCA CTT CAG (SEQ ID NO:35).

The level of binding of an oligonucleotide of set 1 to the tissue sample is compared to the level of binding of an oligonucleotide of set 2 to the tissue sample. A lower level of binding of an oligonucleotide from set 1 compared to that of an oligonucleotide from set 2 indicates the presence of a mutant form of β-APP in the tissue or bodily fluid sample. Thus, utilizing oligonucleotides specifically hybridizable with wild-type βAPP, mutant βAPP is distinguished from wild-type βAPP.

Similarly, the present invention can be used to distinguish β-amyloid-associated conditions from CNS disorders or myositis having other etiologies, in order that an efficacious treatment regime can be designed.

The oligonucleotides of the invention are also useful for detection and diagnosis of abnormal βAPP expression. For example, radiolabeled oligonucleotides can be prepared by $^{32}$P labeling at the 5' end with polynucleotide kinase [Sambrook et al., *Molecular Cloning. A Laboratory Manual*, Cold Spring Harbor Laboratory Press, (1989) Volume 2, pg. 10.59]. Radiolabeled oligonucleotides are then contacted with tissue or cell samples suspected of abnormal βAPP expression and the sample is washed to remove unbound oligonucleotide. Radioactivity remaining in the sample indicates bound oligonucleotide (which in turn indicates the presence of β-amyloid) and can be quantitated using a scintillation counter or other routine means. Abnormally high levels of βAPP expression can be detected in this way. Double-labeling can be used with oligonucleotides and methods of the invention to specifically detect expression of mutated β-amyloid. Radiolabeled oligonucleotide can also be used to perform autoradiography of tissues to determine the localization, distribution and quantitation of abnormal β-amyloid expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing βAPP. Quantitation of the silver grains permits abnormally high levels of β-amyloid expression to be detected.

Analogous assays for detection of fluorescence as a means of assessing β-amyloid expression can be developed using oligonucleotides of the invention which are conjugated to fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 Catalog of Products for DNA Research, Glen Research, Sterling, Va., p. 21). Double labeling can be used with oligonucleotides and methods of the invention to specifically detect expression of mutated β-amyloid. In a similar manner, enzyme-linked assays may also be employed to assess expression or to detect the presence or absence of βAPP.

Each of the assays and yet other assays for detection of gene expression are well known in the art. Those of skill in the art may easily employ these assays for detection of abnormal β-amyloid expression in accordance with the teachings of the invention, thereby providing a novel and useful means to detect β-amyloid expression.

The oligonucleotides of this invention may also be used for research purposes. Thus, the specific hybridization exhibited by the oligonucleotides are useful for assays, purifications, cellular product preparations and in other methodologies which may be appreciated by persons of ordinary skill in the art.

The following examples illustrate the present invention and are not intended to limit the same.

EXAMPLES

Example 1

Synthesis of Oligonucleotides: Unmodified DNA oligonucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle is replaced by a 0.2M solution of 3H-1,2-benzodithiole-3-one 1,1-dioxide in acetonitrile for the stepwise thiation of the phosphite linkages. The thiation cycle wait step is increased to 68 seconds and is followed by the capping step.

2'-O-methyl phosphorothioate oligonucleotides are synthesized using 2'-O-methyl β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. The 3'-base used to start the synthesis is a 2'-deoxyribonucleotide.

After cleavage from the controlled pore glass column (Applied Biosystems, Foster City, Calif.) and deblocking in concentrated ammonium hydroxide at 55° C. for 18 hours, the oligonucleotides are purified by precipitation twice out of 0.5M NaCl with 2.5 volumes ethanol. Analytical gel electrophoresis is accomplished in 20% acrylamide, 8M urea, 45 mM Tris-borate buffer, pH 7.0. Oligodeoxynucleotides and phosphorothioates are judged from electrophoresis to be greater than 80% full length material. Example 2

βAPP-Luciferase Reporter Gene Assembly: The βAAP-luciferase reporter genes described in this study are assembled using PCR technology. The final construct is assembled in two steps. In the first step, oligonucleotide primers are synthesized for use as primers for PCR cloning of the 5'-regions of β-amyloid. The β-amyloid cDNA template is purchased from the American Type Culture Collection (ATCC number 61910) in Bethesda, Md. The oligonucleotide primers used for this step of the cloning procedure are 5'-ACA-TTA-TGC-TAG-CGC-AGC-GGT-AGG-CGA-GAG-CAC-3' (sense; SEQ ID NO: 24) and 5'-GAG-ATC-TGA-AGC-TTC-GTC-CAG-GCG-GCC-AGC-AGG-A-3' (antisense; SEQ ID NO: 25). These primers are used in standard PCR reactions using wild type β-amyloid cDNA as template. These primers are expected to produce a DNA product of 204 base pairs corresponding to sequences +142 to +48 (relative to the translational initiation site) of the βAPP gene, flanked by NheI and HindIII restriction endonuclease sites. This PCR product contains the 5'-nontranslated and translational initiation regions of the βAPP gene. The PCR product is gel purified, precipitated, washed and resuspended in water using standard procedures. This product is then cloned into a steroid-regulatable [mouse mammary tumor virus (MMTV) promoter] luciferase expression plasmid that was constructed using the restriction endonucleases NheI and HindIII.

In the second step of the plasmid construction, primers are synthesized for the cloning of the codon 717 (mutation-sensitive) region of the βAPP gene. The oligonucleotides for PCR used for this step of the cloning procedure are 5'-GAG-ATC-TGA-AGC-TTG-GTG-CAA-TCA-TTG-GAC-TCA-TG-3' (sense; SEQ ID NO: 26) and 5'-GAG-ATC-TGA-AGC-TTA-CCA-CCC-CTC-AGC-ATC-ACC-AAG-GTG-ATG-AC-3' (antisense; SEQ ID NO: 27). These primers are used in standard PCR reactions using the wild type βAPP cDNA as template. These primers are expected to produce a DNA product of 135 base pairs corresponding to sequences +489 to +660 (relative to the translation initiation site) of the βAPP gene, flanked by HindIII restriction sites. Following purification of the PCR product, the DNA insert is cloned into the construct described in step one above using the restriction endonuclease HindIII.

The resulting expression vector encodes a βAPP/ luciferase fusion RNA which is expressed under the control of the steroid-inducible MMTV promoter. Translation of this fusion RNA is dependent on initiation at the βAPP AUG codon. Furthermore, sequences (ACC-ACC-CCT) which encode the protein-processing recognition sequence Arg-Gly-Gly at the βAPP/luciferase fusion site have been incorporated into the step two antisense primer. This sequence is known to be cleaved by specific enzymes following translation to produce the β-amyloid protein fragment and free luciferase. Thus, detection of gene expression using this construct includes measurement of both luciferase and βAPP production and/or activity.

Example 3

Transfection of Cells with Plasmid DNA: Transfections are performed as described by Greenberg [*Current Protocols in Molecular Biology*, F. M. Ausubel, R. Brent, R. E. Kingston, D. D. Moore, J. A. Smith, J. G. Seidman and K. Struhl, eds., John Wiley and Sons, NY], with the following modifications. HeLa cells are plated on 60 mm dishes at $5 \times 10^5$ cells/dish. A total of 10 µg of DNA is added to each dish, of which 9 µg is βAPP-luciferase reporter plasmid and 1 µg is a vector expressing the rat glucocorticoid receptor under control of the constitutive Rous sarcoma virus (RSV) promoter. Calcium phosphate-DNA coprecipitates are removed after 16–20 hours by washing with Tris-buffered saline [50 Mm Tris-Cl (pH 7.5), 150 mM NaCl] containing 3 mM EGTA. Fresh medium supplemented with 10% fetal bovine serum is then added to the cells. At this time, cells are pre-treated with antisense oligonucleotides prior to activation of reporter gene expression by dexamethasone.

Example 4

Oligonucleotide Treatment of Cells: Immediately following plasmid transfection, cells are washed three times with Opti-MEM (GIBCO-BRL), prewarmed to 37° C. Two ml of Opti-MEM containing 10 µg/ml N-[1-(2,3-dioleyloxy)propyl]-N,N,N,-trimethylammonium chloride (DOTMA) (Bethesda Research Laboratories, Gaithersburg, Md.) is added to each dish and oligonucleotides are added directly and incubated for 4 hours at 37° C. Opti-MEM is then removed and replaced with the appropriate cell growth medium containing oligonucleotide. At this time, reporter gene expression is activated by treatment of cells with dexamethasone to a final concentration of 0.2 µM. Cells are harvested at 12–16 hours following steroid treatment.

Example 5

Luciferase Assays: Luciferase is extracted from cells by lysis with the detergent Triton X-100, as described by Greenberg [*Current Protocols in Molecular Biology*, F. M. Ausubel, R. Brent, R. E. Kingston, D. D. Moore, J. A. Smith, J. G. Seidman and K. Strahl, eds., John Wiley and Sons, NY]. A Dynatech ML1000 luminometer is used to measure peak luminescence upon addition of luciferin (Sigma) to 625 µM. For each extract, luciferase assays are performed multiple times, using differing amounts of extract to ensure that the data are gathered in the linear range of the assay.

Example 6

Antisense Oligonucleotide Inhibition of βAPP-Luciferase Gene Expression: A series of antisense phosphorothioate oligonucleotides targeted to the translation initiation codon of the βAPP gene are screened using the βAPP-luciferase reporter gene system described in the foregoing examples. The base sequences and sequence ID numbers of these oligonucleotides are shown in Table 2.

TABLE 2

| SEQ ID NO: | SEQUENCE: | | | | | |
|---|---|---|---|---|---|---|
| 1 | GCC | AAA | CCG | GGC AGC | ATC | GC |
| 2 | AGC | ATC | GCG | ACC CTG | CGC | GG |
| 3 | AAA | CCG | GGC | AGC ATC | GCG | AC |

Example 7

Antisense inhibition of βAPP-luciferase expression using gapped 2'-O-methyl phosphorothioate oligonucleotides: A series of oligonucleotides were designed having phosphorothioate linkages throughout the molecule, and also having 2'-O-methyl nucleotide modifications on at least one base at the 5'- and 3'-termini. The result is a phosphorothioate, 2'-O-methylated oligonucleotide having a "gap" in the 2'-O-methyl modifications (the nucleotides in the "gap" region are 2'-deoxynucleotides). Because 2'-O-methylated nucleotides are resistant to RNase H cleavage, the deoxy "gap" permits RNase H cleavage to be directed to this region of the oligonucleotide, and thus to the desired region (here the AUG) of the target mRNA.

These oligonucleotides are shown in Table 3:

TABLE 3

GAPPED 2'-O-METHYL PHOSPHOROTHIOATE OLIGONUCLEOTIDES TARGETED TO THE AUG REGION OF THE βAPP mRNA
(Phosphorothioates throughout; 2'-O-methyl nucleotides shown in bold)

| SEQ ID NO | SEQUENCE | | | | | |
|---|---|---|---|---|---|---|
| 1 | GCC | AAA | CCG | GGC AGC | ATC | GC |
| 2 | AGC | ATC | GCG | ACC CTG | CGC | GG |
| 3 | AAA | CCG | GGC | AGC ATC | GCG | AC |

Example 8

Antisense oligonucleotide inhibition of expression of the mutated βAPP-Luciferase gene having a G-to-A mutation at codon 717: A series of antisense phosphorothioate oligonucleotides targeted to codon 717 of the mutated βAPP gene in which a G-to-A mutation at this codon results in a valine-to-isoleucine mutation [Goate et al. (1991) *Nature* 349:704–706] are screened using the βAPP-luciferase reporter gene system described in the foregoing examples. The base sequences and sequence ID numbers of these oligonucleotides are shown in Table 4.

TABLE 4

OLIGONUCLEOTIDES TARGETED TO THE G-to-A MUTATION OF MUTATED βAPP CODON 717

| SEQ ID NO | SEQUENCE | | | | | |
|---|---|---|---|---|---|---|
| 4 | GTG | ATG | ATG | ATC | ACT | |
| 5 | GGT | GAT | GAT | GAT | CAC | TG |
| 6 | AGG | TGA | TGA | TGA | TCA | CTG T |
| 7 | AAG | GTG | ATG | ATG | ATC | ACT GTC |

Example 9

Antisense inhibition of mutated βAPP-luciferase expression using gapped 2'-O-methyl phosphorothioate oligonucleotides: A series of oligonucleotides were designed having phosphorothioate linkages throughout, and also having 2'-O-methyl nucleotide modifications on at least one base at the 5'- and 3'-termini. The result is a phosphorothioate, 2'-O-methylated oligonucleotide having a "gap" in the 2'-O-methyl modifications (the nucleotides in the "gap" region are 2'-deoxynucleotides). Because 2'-O-methylated nucleotides are resistant to RNase H cleavage, the deoxy "gap" permits RNase H cleavage to be directed to this region of the oligonucleotide, and thus to the desired region of the target mRNA (here the G-to-A mutation at codon 717).

These oligonucleotides are shown in Table 5.

TABLE 5

GAPPED 2'-O-METHYL PHOSPHOROTHIOATE OLIGO-
NUCLEOTIDES TARGETED TO CODON 717 OF THE MUTATED
βAPP mRNA
(Phosphorothioates throughout; 2'-O-Methyl
nucleotides shown in bold)

| SEQ ID NO | SEQUENCE | | | | | |
|---|---|---|---|---|---|---|
| 4 | GTG | ATG | ATG | ATC | ACT | |
| 5 | GGT | GAT | GAT | GAT | CAC | TG |
| 6 | AGG | TGA | TGA | TGA | TCA | CTG T |
| 7 | AAG | GTG | ATG | ATG | ATC | ACT GTC |

Example 10

Antisense oligonucleotide inhibition of expression of the mutated βAPP-Luciferase Gene having a G-to-T mutation at codon 717: A series of antisense phosphorothioate oligonucleotides targeted to codon 717 of the mutated βAPP gene in which a G-to-T mutation at this codon results in a valine-to-phenylalanine mutation [Murrell et al. (1991) Science 254:97–99] are screened using the βAPP-luciferase reporter gene system described in the foregoing examples. The base sequences and sequence ID numbers of these oligonucleotides are shown in Table 6.

TABLE 6

OLIGONUCLEOTIDES TARGETED TO THE
G-to-T MUTATION OF βAPP

| SEQ ID NO | SEQUENCE | | | | | |
|---|---|---|---|---|---|---|
| 8 | GTG | ATG | AAG | ATC | ACT | |
| 9 | GGT | GAT | GAA | GAT | CAC | TG |
| 10 | AGG | TGA | TGA | AGA | TCA | CTG T |
| 11 | AAG | GTG | ATG | AAG | ATC | ACT GTC |

Example 11

Antisense inhibition of mutated βAPP-luciferase expression using gapped 2'-O-methyl phosphorothioate oligonucleotides: A series of oligonucleotides were designed having phosphorothioate linkages throughout, and also having 2'-O-methyl nucleotide modifications on at least one base at the 5'- and 3'-termini. The result is a phosphorothioate, 2'-O-methylated oligonucleotide having a "gap" in the 2'-O-methyl modifications (the nucleotides in the "gap" region are 2'-deoxynucleotides). Because 2'-O-methylated nucleotides are resistant to RNase H cleavage, the deoxy "gap" permits RNase H cleavage to be directed to this region of the oligonucleotide, and thus to the desired region of the target mRNA (here the G-to-T mutation at codon 717).

These oligonucleotides are shown in Table 7:

TABLE 7

GAPPED 2'-O-METHYL PHOSPHOROTHIOATE OLIGO-
NUCLEOTIDES TARGETED TO CODON 717 REGION OF
MUTATED βAPP mRNA
(Phosphorothioates throughout; 2'-O-Methyl
nucleotides shown in bold)

| SEQ ID NO | SEQUENCE | | | | | |
|---|---|---|---|---|---|---|
| 8 | GTG | ATG | AAG | ATC | ACT | |
| 9 | GGT | GAT | GAA | GAT | CAC | TG |
| 10 | AGG | TGA | TGA | AGA | TCA | CTG T |
| 11 | AAG | GTG | ATG | AAG | ATC | ACT GTC |

Example 12

Antisense oligonucleotide inhibition of mutated βAPP-Luciferase Gene Expression: A series of antisense phosphorothioate oligonucleotides targeted to codon 717 of the mutated βAPP gene in which a T-to-G mutation at this codon results in a valine-to-glycine mutation [Chartier-Harlin et al. (1991) Nature 353:844–846] are screened using the βAPP-luciferase reporter gene system described in the foregoing examples. The base sequences and sequence ID numbers of these oligonucleotides are shown in Table 8.

TABLE 8

OLIGONUCLEOTIDES TARGETED TO THE
T-to-G MUTATION OF βAPP

| SEQ ID NO | SEQUENCE | | | | | |
|---|---|---|---|---|---|---|
| 12 | GTG | ATG | CCG | ATC | ACT | |
| 13 | GGT | GAT | GCC | GAT | CAC | TG |
| 14 | AGG | TGA | TGC | CGA | TCA | CTG T |
| 15 | AAG | GTG | ATG | CCG | ATC | ACT GTC |

Example 13

Antisense inhibition of mutated βAPP-luciferase expression using gapped 2'-O-methyl phosphorothioate oligonucleotides: A series of oligonucleotides were designed having phosphorothioate linkages throughout, and also having 2'-O-methyl nucleotide modifications on at least one base at the 5'- and 3'-termini. The result is a phosphorothioate, 2'-O-methylated oligonucleotide having a "gap" in the 2'-O-methyl modifications (the nucleotides in the "gap" region are 2'-deoxynucleotides). Because 2'-O-methylated nucleotides are resistant to RNase H cleavage, the deoxy "gap" permits RNase H cleavage to be directed to this region of the oligonucleotide, and thus to the desired region of the target mRNA (here the T-to-G mutation at codon 717).

These oligonucleotides are shown in Table 9:

TABLE 9

GAPPED 2'-O-METHYL PHOSPHOROTHIOATE OLIGO-
NUCLEOTIDES TARGETED TO CODON 717 OF MUTATED
βAPP mRNA
(Phosphorothioates throughout; 2'-O-Methyl
nucleotides shown in bold)

| SEQ ID NO | SEQUENCE | | | | | |
|---|---|---|---|---|---|---|
| 12 | GTG | ATG | CCG | ATC | ACT | |
| 13 | GGT | GAT | GCC | GAT | CAC | TG |

TABLE 9-continued

GAPPED 2'-O-METHYL PHOSPHOROTHIOATE OLIGO-
NUCLEOTIDES TARGETED TO CODON 717 OF MUTATED
βAPP mRNA
(Phosphorothioates throughout; 2'-O-Methyl
nucleotides shown in bold)

| SEQ ID NO | SEQUENCE | | | | | | |
|---|---|---|---|---|---|---|---|
| 14 | AGG | TGA | TGC | CGA | TCA | CTG | T |
| 15 | AAG | GTG | ATG | CCG | ATC | ACT | GTC |

Example 14

Cell culture and treatment with oligonucleotides: Human umbilical vein endothelial cells (HUVEC) (Clonetics, San Diego, Calif.) are cultured in EGM-U medium (Clonetics). Cells are used between the second and sixth passages. Cells grown in 96-well plates are washed three times with Opti-MEM (GIBCO, Grand Island, N.Y.) prewarmed to 37° C. 100 μl of Opti-MEM containing either 10 μg/ml N-[1-(2,3-dioleyloxy)propyl]-N,N,N-trimethylammonium chloride (DOTMA, Bethesda Research Laboratories, Bethesda, Md.) is added to each well. Oligonucleotides are sterilized by centrifugation through 0.2 μm Centrex cellulose acetate filters (Schleicher and Schuell, Keene, N.H.). Oligonucleotides are added as 20x stock solution to the wells and incubated for 4 hours at 37° C. Medium is removed and replaced with 150 μl of the appropriate growth medium containing the indicated concentration of oligonucleotide. The presence of DOTMA during the first 4 hours incubation with oligonucleotide increased the potency of the oligonucleotides at least 100-fold. This increase in potency correlated with an increase in uptake of the oligonucleotide by cells.

Example 15

ELISA screening of antisense oligonucleotides for activity against βAPP gene expression in HUVEC cells: Expression of βAPP by HUVEC cells can be quantitated using specific antibodies (Anti-β-Amyloid, Boehringer Mannheim) in an ELISA. Cells are grown to confluence in 96 well microtiter plates and gently washed three times with a buffered isotonic solution containing calcium and magnesium such as Dulbecco's phosphate buffered saline (D-PBS). The cells are then directly fixed on the microtiter plate with 1 to 2% paraformaldehyde diluted in D-PBS for 20 minutes at 25° C. The cells are washed again with D-PBS three times. Nonspecific binding sites on the microtiter plate are blocked with 2% bovine serum albumin in D-PBS for 1 hour at 37° C. Cells are incubated with the antibody diluted in blocking solution for 1 hour at 37° C. Unbound antibody is removed by washing the cells three times with D-PBS. Antibody bound to the cells is detected by incubation with a 1:1000 dilution of biotinylated goat anti-mouse IgG (Bethesda Research Laboratories, Gaithersburg, Md.) in blocking solution for 1 hour at 37° C. Cells are washed three times with D-PBS and then incubated with a 1:1000 dilution of streptavidin conjugated to β-galactosidase (Bethesda Research Laboratories) for 1 hour at 37° C. The cells are washed three times with D-PBS for 5 minutes each. The amount of β-galactosidase bound to the specific antibody is determined by developing the plate in a solution of 3.3 mM chlorophenolred-β-D-galactopyranoside, 50 mM sodium phosphate, 1.5 mM MgCl$_2$; pH=7.2 for 2 to 15 minutes at 37° C. The concentration of the product is determined by measuring the absorbance at 575 nm in an ELISA microtiter plate reader.

Example 16

Intrathecal administration of oligonucleotides: A catheter is surgically inserted into the L3–4 lumbar spinal interspace of a human patient, and is connected to a subcutaneous infusion pump (Medtronic Inc., Minneapolis, Minn.) which has been surgically implanted in the upper abdominal region [Lewis and Mueller (1993) *The Annals of Pharmacotherapy* 27:767–774; Luer and Hatton (1993) *The Annals of Pharmacotherapy* 27:912–921; Ettinger et al. (1978) *Cancer* 41:1270–1273]. The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and dosage, ranging from 1 μg to 1 kg, of drug to be administered, the pump reservoir may be refilled at 3–10 week intervals. Refilling of the pump is accomplished by a single percutaneous puncture to the self-sealing septum.

Example 17

Detection of abnormal βAPP expression: Oligonucleotides are radiolabeled after synthesis by $^{32}$P labeling at the 5' end with polynucleotide kinase [Sambrook et al., *Molecular Cloning. A Laboratory Manual*, Cold Spring Harbor Laboratory Press, 1989, Volume 2, pg. 11.31–11.32]. Radiolabeled oligonucleotides are contacted with tissue or cell samples suspected of abnormal βAPP expression under conditions in which specific hybridization can occur, and the sample is washed to remove unbound oligonucleotide. Radioactivity remaining in the sample indicates bound oligonucleotide and is quantitated using a scintillation counter or other routine means.

Radiolabeled oligonucleotides of the invention are also used in autoradiography. Tissue sections are treated with radiolabeled oligonucleotide and washed as described above, then exposed to photographic emulsion according to standard autoradiography procedures. The emulsion, when developed, yields an image of silver grains over the regions expressing abnormal βAPP. The extent of abnormal βAPP expression is determined by quantitation of the silver grains.

Analogous assays for fluorescent detection of abnormal βAPP expression use oligonucleotides of the invention which are labeled with fluorescein or other fluorescent tags. Labeled oligonucleotides are synthesized on an automated synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling Va.). Incubation of the oligonucleotide and the biological sample is carried out as described for radiolabeled oligonucleotides except that instead of a scintillation counter, a fluorimeter or fluorescence microscope is used to detect fluorescence which is indicative of βAPP expression.

Example 18

Detection of expression of mutated βAPP: Tissue or cell samples suspected of expressing mutated βAPP are incubated with a $^{32}$P or fluorescein-labeled oligonucleotide which is targeted to codon 717 (or alternatively, codons 670 and/or 671) of wild type βAPP mRNA. An identical sample of cells or tissues is incubated with a second labeled oligonucleotide which is targeted to the translation initiation site of wild type βAPP mRNA, under conditions in which specific hybridization can occur, and the sample is washed to remove unbound oligonucleotide. Label remaining in the sample indicates bound oligonucleotide and can be quantitated using a scintillation counter, fluorimeter, or other routine means. The presence of mutated βAPP is indicated if binding is observed in the case of the second but not the first sample. Alternatively, the first oligonucleotide can be targeted to mutated codon 717 (or codons 670 and/or 671) and the second oligonucleotide is targeted to the normal wild type βAPP AUG. In this case, the presence of mutated βAPP is indicated if both oligonucleotides bind (i.e. both samples are radioactive).

Double labeling can also be used with the oligonucleotides and methods of the invention to specifically detect expression of mutated βAPP. A single tissue sample is incubated with a $^{32}$P labeled oligonucleotide which is targeted to codon 717 (or alternatively, codons 670 and/or 671) of wild type βAPP mRNA and a fluorescein-labeled oligonucleotide which is targeted to the translation initiation site of wild type βAPP mRNA, under conditions in which specific hybridization can occur. The sample is washed to remove unbound oligonucleotide and labels are detected by scintillation counting and fluorimetry. The presence of mutated βAPP is indicated if the sample does not bind the $^{32}$P-labeled oligonucleotide (i.e., is not radioactive) but does retain the fluorescent label. Alternatively, the first oligonucleotide can be targeted to mutated codon 717 (or codons 670 and/or 671) and the second oligonucleotide is targeted to the wild type βAPP AUG. In this case, the presence of mutated βAPP is indicated if the sample binds both oligonucleotides, i.e. is both radioactive and fluorescent.

Example 19

Antisense oligonucleotide inhibition of expression of the mutated βAPP-Luciferase gene having G-to-T and A-to-C mutations at codons 670 and 671, respectively: A series of antisense phosphorothioate oligonucleotides targeted to codons 670 and 671 of the mutated βAPP gene in which a G-to-T mutation results in a lysine-to-asparagine mutation and a A-to-C mutation results in a methionine-to-leucine mutation [Mullan, et al. (1992) Nature Genetics 1:345–347] are screened using the βAPP-luciferase reporter gene system described in the foregoing examples. The sequence of the oligonucleotides [based on the βAPP sequence according to Kang, et al. (1987) Nature 325:733–736] and their respective sequence ID numbers are shown in Table 10.

TABLE 10

OLIGONUCLEOTIDES TARGETED TO THE G-TO-T AND A-TO-C MUTATIONS OF βAPP CODONS 670 AND 671

| SEQ ID NO | SEQUENCE | | | | | |
|---|---|---|---|---|---|---|
| 28 | GCA | TCC | AGA | TTC | ACT | |
| 29 | CAT | CCA | GAT | TCA | CTT | |
| 30 | TGC | ATC | CAG | ATT | CAC | TT |
| 31 | GCA | TCC | AGA | TTC | ACT | TC |
| 32 | CTG | CAT | CCA | GAT | TCA | CTT C |
| 33 | TGC | ATC | CAG | ATT | CAC | TTC A |
| 34 | TCT | GCA | TCC | AGA | TTC | ACT TCA |
| 35 | CTG | CAT | CCA | GAT | TCA | CTT CAG |

Example 20

Antisense inhibition of mutated βAPP-luciferase expression using gapped 2'-O-methyl phosphorothioate oligonucleotides: A series of oligonucleotides were designed having phosphorothioate linkages throughout, and also having 2'-O-methyl nucleotide modifications on at least one base at the 5'- and 3'-termini. The result is a phosphorothioate, 2'-O-methylated oligonucleotide having a "gap" in the 2'-O-methyl modifications (the nucleotides in the "gap" region are 2'-deoxynucleotides). Because 2'-O-methylated nucleotides are resistant to RNase H cleavage, the deoxy "gap" permits RNase H cleavage to be directed to this region of the oligonucleotide, and thus to the desired region of the target mRNA (here the G-to-T and A-to-C mutations at codons 670 and 671, respectively).

These oligonucleotides are shown in Table 11:

TABLE 11

GAPPED 2'-O-METHYL PHOSPHOROTHIOATE OLIGO-
NUCLEOTIDES TARGETED TO CODONS 670 AND 671 OF THE
MUTATED βAPP mRNA
(Phosphorothioates throughout; 2'-O-Methyl
nucleotides shown in bold)

| SEQ ID NO | SEQUENCE | | | | | |
|---|---|---|---|---|---|---|
| 28 | GCA | TCC | AGA | TTC | ACT | |
| 29 | CAT | CCA | GAT | TCA | CTT | |
| 30 | TGC | ATC | CAG | ATT | CAC | TT |
| 31 | GCA | TCC | AGA | TTC | ACT | TC |
| 32 | CTG | CAT | CCA | GAT | TCA | CTT C |
| 33 | TGC | ATC | CAG | ATT | CAC | TTC A |
| 34 | TCT | GCA | TCC | AGA | TTC | ACT TCA |
| 35 | CTG | CAT | CCA | GAT | TCA | CTT CAG |

Example 21

Intraventricular administration of oligonucleotides: A silicon catheter is surgically introduced into a ventricle of the brain of a human patient, and is connected to a subcutaneous infusion pump that has been surgically implanted in the abdominal region [Zimm et al. (1984) Cancer Research 44:1698–1701]. The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and dosage of drug to be administered, ranging from 1 βg to 1 kg, the pump reservoir may be refilled at 3–10 week intervals. Refilling of the pump is accomplished by percutaneous puncture of the self-sealing septum of the pump.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An oligonucleotide consisting of 8 to 50 nucleotides comprising a nucleotide sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:28, SEQ ID NO:29, SEQ ID NO:30, SEQ ID NO:31, SEQ ID NO:32, SEQ ID NO:33, SEQ ID NO:34, SEQ ID NO:35, wherein said oligonucleotide is specifically hybridizable with a nucleic acid encoding an abnormally expressed β-amyloid precursor protein, and wherein at least one of the linkages between the nucleotides of said oligonucleotide is a phosphorothioate linkage.

2. An oligonucleotide consisting of 8 to 50 nucleotides comprising a nucleotide sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:28, SEQ ID NO:29, SEQ ID NO:30, SEQ ID NO:31, SEQ ID NO:32, SEQ ID NO:33, SEQ ID NO:34, SEQ ID NO:35, wherein said oligonucleotide is specifically hybridizable with a nucleic acid encoding an abnormally expressed β-amyloid precursor protein, and wherein at least one of the nucleotides comprises a 2'-O-alkyl moiety.

3. An oligonucleotide consisting of 8 to 50 nucleotides comprising a nucleotide sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:28, SEQ ID NO:29, SEQ ID NO:30, SEQ ID NO:31, SEQ ID NO:32, SEQ ID NO:33, SEQ ID NO:34, SEQ ID NO:35, wherein said oligonucleotide is specifically hybridizable with a nucleic acid encoding an abnormally expressed β-amyloid precursor protein, and wherein at least one of the nucleotides comprises a 2'-O-methyl moiety.

* * * * *

UNITED STATES PATENT AND TRADEMARK OFFICE
CERTIFICATE OF CORRECTION

PATENT NO. : 5,837,449
DATED : November 17, 1998
INVENTOR(S) : Monia et al.

It is certified that error appears in the above-indentified patent and that said Letters Patent is hereby corrected as shown below:

Column 5-6, in Table 1, delete "(SEQ ID NO:52" and substitute therefor --(SEQ ID NO:52) --;
Column 5-6, in Table 1, delete "(SEQ ID NO:53" and substitute therefor --(SEQ ID NO:53) --;
Column 7, line 7, delete "asZ" and substitute therefor -- as --;
Column 7, line 41, "`Hybridization.'" should begin a new paragraph;
Column 8, line 48, delete "13";
Column 8, line 51, delete first occurrence of "No.";
Column 14, line 24, "Example 2" should begin a new line;
Column 14, line 25, delete "βAAP" and substitute therefor -- βAPP --;
Column 14, line 41, delete "+142" and substitute therefor -- -142 --;
Column 19, line 17, delete "EGM-U" and substitute therefor -- EGM-UV --;
Column 22, line 54, delete "1βg" and substitute therefor -- 1µg --;
Column 43, lines 7-8, delete "SEQ ID NO:29, SEQ ID NO:30, SEQ ID NO:31";
Column 43, line 9, delete "SEQ ID NO:33" ;
Column 43, line 9, insert between "SEQ ID NO:34" and "SEQ ID NO:35" the word -- and --;

UNITED STATES PATENT AND TRADEMARK OFFICE
CERTIFICATE OF CORRECTION

PATENT NO. : 5,837,449
DATED : November 17, 1998
INVENTOR(S) : Monia et al.

It is certified that error appears in the above-indentified patent and that said Letters Patent is hereby corrected as shown below:

Column 43, line 19, delete "SEQ ID";
Column 44, lines 1-2, delete "NO:29, SEQ ID NO:30, SEQ ID NO:31";
Column 44, line 2, insert between "SEQ ID NO:34" and "SEQ ID NO:35" the word -- and --;
Column 44, lines 12-13, delete "SEQ ID NO:29, SEQ ID NO:30, SEQ ID NO:31";
Column 44, line 14, delete "SEQ ID NO:33";
Column 44, line 14, insert between "SEQ ID NO:34"; and "SEQ ID NO:35" the word -- and --;

Column 23, Sequence Listing, under "General Information" please insert subsections (i), (ii), (iv), (v), (vi), (vii), (viii) and (ix)

Signed and Sealed this

Twentieth Day of June, 2000

Attest:

Q. TODD DICKINSON

*Attesting Officer*     *Director of Patents and Trademarks*